(12) United States Patent
Ratner et al.

(10) Patent No.: US 7,972,628 B2
(45) Date of Patent: Jul. 5, 2011

(54) POROUS BIOMATERIALS

(75) Inventors: Buddy D. Ratner, Seattle, WA (US);
Andrew Marshall, Federal Way, WA (US)

(73) Assignee: University of Washington, Seattle, WA (US)

( * ) Notice: Subject to any disclaimer, the term of this patent is extended or adjusted under 35 U.S.C. 154(b) by 1138 days.

(21) Appl. No.: 10/595,233

(22) PCT Filed: Oct. 1, 2004

(86) PCT No.: PCT/US2004/032639
§ 371 (c)(1),
(2), (4) Date: Jan. 23, 2007

(87) PCT Pub. No.: WO2005/032418
PCT Pub. Date: Apr. 14, 2005

(65) Prior Publication Data
US 2008/0075752 A1    Mar. 27, 2008

Related U.S. Application Data

(60) Provisional application No. 60/507,734, filed on Oct. 1, 2003.

(51) Int. Cl.
*A61K 9/50*    (2006.01)
(52) U.S. Cl. ......................... 424/499; 424/501
(58) Field of Classification Search .................. None
See application file for complete search history.

(56) References Cited

U.S. PATENT DOCUMENTS

| | | | |
|---|---|---|---|
| 5,410,016 | A | 4/1995 | Hubbell |
| 5,681,572 | A | 10/1997 | Seare, Jr. |
| 6,261,585 | B1 | 7/2001 | Sefton |
| 6,471,993 | B1 | 10/2002 | Shastri |
| 6,656,496 | B1 | 12/2003 | Kilpadi |
| 6,702,848 | B1 | 3/2004 | Zilla |
| 6,702,857 | B2 | 3/2004 | Brauker |
| 7,192,450 | B2 | 3/2007 | Brauker |

FOREIGN PATENT DOCUMENTS

| | | |
|---|---|---|
| WO | 00/34454 A2 | 6/2000 |
| WO | 01/05333 A1 | 1/2001 |

OTHER PUBLICATIONS

"Thermoplastic polymers", Wkikipedia.com, Aug. 11, 2010.*
Borden, M., et al., "Tissue Engineered Microsphere-Based Matrices for Bone Repair: Design and Evaluation," Biomaterials 23(2):551-559, Jan. 2002.

(Continued)

*Primary Examiner* — Carlos Azpuru
(74) *Attorney, Agent, or Firm* — Christensen O'Connor Johnson Kindness PLLC (57) ABSTRACT

The invention provides porous biomaterials and methods for forming porous biomaterials. The porous biomaterials of the invention comprise a biocompatible polymer scaffold defining an array of pores, wherein substantially all the pores have a similar diameter, wherein the mean diameter of the pores is between about 20 and about 90 micrometers, wherein substantially all the pores are each connected to at least 4 other pores, and wherein the diameter of substantially all the connections between the pores is between about 15% and about 40% of the mean diameter of the pores. The invention also provides implantable devices comprising a layer of a biomaterial, and methods for promoting angiogenesis in and around an implantable biomaterial.

20 Claims, 2 Drawing Sheets

OTHER PUBLICATIONS

Brauker, J.H., et al., "Neovascularization of Synthetic Membranes Directed by Membrane Microarchitecture," Journal of Biomedical Materials Research 29(12):1517-1524, Dec. 1995.

Supplementary International Search Report mailed Oct. 20, 2009, issued in corresponding International Application No. PCT/US2004/032639, filed Oct. 1, 2004.

Sharkawy, A.A., "Engineering the Tissue Which Encapsulates Subcutaneous Implants," Journal of Biomedical Materials Research 40(4):586-597, Jun. 1998.

Bezuidenhout, D., et al., "Effect of Well Defined Dodecahedral Porosity on Inflammation and Angiogenesis," ASAIO (American Society for Artificial Internal Organs) Journal 48(5):465-471, Sep./Oct. 2002.

Communication Pursuant to Article 94(3) EPC mailed Feb. 15, 2011, issued in corresponding European Patent Application No. 04 794 111.7, filed Oct. 1, 2004, 5 pages.

Clubb, Jr., F.J., et al., "Surface Texturing and Coating of Biomaterial Implants: Effects on Tissue Integration and Fibrosis," ASAIO [American Society of Artificial Internal Organs] Journal 45(4):281-287, Jul.-Aug. 1999.

* cited by examiner

POROUS BIOMATERIALS

CROSS-REFERENCE TO RELATED APPLICATION

This application claims the benefit of U.S. Provisional Application No. 60/507,734, filed Oct. 1, 2003.

GOVERNMENT RIGHTS

This invention was made with government support under EEC-9529161 awarded by the National Science Foundation and under R24HL 64387 awarded by the National Institutes of Health. The government has certain rights in the invention.

FIELD OF THE INVENTION

The present invention relates to porous biomaterials that support the in-growth of blood vessels, and implantable devices comprising them. The invention also relates to methods for forming and using the porous biomaterials of the invention.

BACKGROUND OF THE INVENTION

Porous biomaterials are used in a variety of implantable medical devices, including sutures and vascular grafts. Implants frequently induce a foreign body response that results in the formation of an avascular, fibrous capsule around the implant, which limits the performance of many implants. It has been shown that the biological response to implanted biomaterials is dependent on the microarchitecture of the biomaterial (see, e.g., Brauker et al. (1995) *J. Biomed. Mater. Res.* 29(12):1517-24; Sharkawy et al. (1998) *J. Biomed. Mater. Res.* 40:586-97). There is a continuing need for porous biomaterials that promote vascularization in and around the implant and reduce the foreign body reaction.

SUMMARY OF THE INVENTION

In one aspect, the invention provides porous biomaterials. The porous biomaterials of the invention comprise a biocompatible polymer scaffold defining an array of pores, wherein substantially all the pores have a similar diameter, wherein the mean diameter of the pores is between about 20 and about 90 micrometers, wherein substantially all the pores are each connected to at least 4 other pores, and wherein the diameter of substantially all the connections between the pores is between about 15% and about 40% of the mean diameter of the pores. In some embodiments, the mean diameter of the pores is between about 30 and 40 micrometers.

The biocompatible polymer scaffold of the biomaterials of the invention may comprise any biocompatible polymer, such as synthetic polymers, naturally-occurring polymers, or mixtures thereof. For example, the biocompatible scaffold may be a hydrogel. In some embodiments, the biocompatible polymer scaffold is degradable. Exemplary biocompatible polymers in the biocompatible polymer scaffolds include, but are not limited to, 2-hydroxyethyl methacrylate, silicone rubber, poly(ε-caprolactone) dimethylacrylate, and collagen. Generally, the polymer scaffold has a low level of microporosity. In some embodiments, the biomaterial of the invention has a thickness of at least 70 micrometers.

The pores in the biomaterials of the invention may have any suitable shape, such as roughly or perfectly spherical. In some embodiments, substantially all the pores are connected to between about 4 to about 12 other pores, such as between about 4 to about 7 other pores.

In some embodiments, the invention provides implantable devices comprising a layer of a biomaterial. The implantable devices may be any implantable medical devices. The devices of the invention comprise a device body, wherein the porous biomaterial is attached to the device body.

Another aspect of the invention provides methods for forming porous biomaterials. The methods comprise the steps of: (a) forming a biocompatible polymer scaffold around a template comprising an array of monodisperse porogens, wherein substantially all the porogens have a similar diameter, wherein the mean diameter of the porogens is between about 20 and about 90 micrometers, wherein substantially all porogens are each connected to at least 4 other porogens, and wherein the diameter of substantially all the connections between the porogens is between about 15% and about 40% of the mean diameter of the porogens; and (b) removing the template to produce a porous biomaterial. Exemplary porogens that are suitable for use in the methods of the invention include, but are not limited to, polymer particles such as PMMA beads and polystyrene beads. In some embodiments, the mean diameter of the porogens is between about 30 and 40 micrometers.

In some embodiments, step (a) of the methods for forming porous biomaterials comprises forming the template by packing the porogens into a mold and fusing the porogens to form connections between the porogens. In some embodiments, the template is removed by solvent extraction after the biocompatible polymer scaffold has been formed.

In a further aspect, the invention provides methods for promoting angiogenesis in and around an implantable biomaterial. The methods comprise the step of implanting a porous biomaterial, wherein the biomaterial comprises a biocompatible polymer scaffold surrounding an array of pores, wherein substantially all the pores have a similar diameter, wherein the mean diameter of the pores is between about 20 and about 90 micrometers, wherein substantially all pores are each connected to at least 4 other pores, and wherein the diameter of substantially all the connections between the pores is between about 15% and about 40% of the mean diameter of the pores.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION OF THE PREFERRED EMBODIMENT

Unless specifically defined herein, all terms used herein have the same meaning as they would to one skilled in the art of the present invention.

One aspect of the invention provides porous biomaterials. The porous biomaterials of the invention comprise a biocompatible polymer scaffold defining an array of pores, wherein substantially all the pores have a similar diameter, wherein the mean diameter of the pores is between about 20 and about 90 micrometers, wherein substantially all the pores are each connected to at least 4 other pores, and wherein the diameter of substantially all the connections between the pores is between about 15% and about 40% of the mean diameter of the pores. In some embodiments, the biomaterial has a thickness of at least 70 micrometers. For example, the biomaterials may have a thickness between about 100 and 1000 micrometers, such as between about 100 micrometers and about 500 micrometers.

The polymer scaffold of the biomaterials of the invention may comprise any biocompatible polymer, such as synthetic polymers, naturally-occurring polymers, or mixtures thereof. Exemplary synthetic biocompatible polymers include, but are not limited to, 2-hydroxyethyl methacrylate (HEMA), silicone rubber, poly($\epsilon$-caprolactone) dimethylacrylate, polysulfone, (poly)methy methacrylate (PMMA), soluble Teflon-AF, (poly) ethylenetetrapthalate (PET, Dacron), Nylon, polyvinyl alcohol, polyurethane, and mixtures thereof. Exemplary naturally-occurring biocompatible polymers include, but are not limited to, fibrous or globular proteins, complex carbohydrates, glycosaminoglycans, or mixtures thereof. Thus, the polymer scaffold may include collagens of all types, elastin, hyaluronic acid, alginic acid, desmin, versican, matricelluar proteins such as SPARC (osteonectin), osteopontin, thrombospondin 1 and 2, fibrin, fibronectin, vitronectin, albumin, etc. Natural polymers may be used as the scaffold or as an additive to improve the biocompatibility of a synthetic polymer.

The polymer scaffold may be a hydrogel. For example, the polymer scaffold may comprise a degradable hydrogel, for example by reacting low-molecular-weight poly($\epsilon$-caprolactone) diol with an excess of methacryloyl chloride to give a polyester with methacrylate endgroups, and copolymerizing this compound with 2-hydroxyethyl methacrylate (HEMA) to yield a cross-linked hydrogel with hydrolyzable linkages, as described in EXAMPLE 1.

The polymer scaffold generally has a low level of microporosity. The term "microporosity" is a measure of the presence of small micropores within the polymer scaffold itself (as opposed to the pores defined by the scaffold). In some embodiments, all or substantially all of the micropores in the polymer scaffold are between about 0.1 micrometers and about 5 micrometers, such as between about 0.1 micrometers and about 3 micrometers or between about 0.1 micrometers and about 2 micrometers. The term "low level of microporosity" means that micropores represent less than 2% of the volume of the polymer scaffold, as measured by measuring the percentage void space in a cross-section through the polymer scaffold.

According to the invention, substantially all the pores in the biomaterial have a similar diameter. As used herein, the term "substantially all the pores" refers to at least 90% of the pores in the biomaterial, such as at least 95% or at least 97% of the pores. The term "diameter of a pore" refers to the longest line segment that can be drawn that connects two points within the pore, regardless of whether the line passes outside the boundary of the pore.

Two pores have a "similar diameter" when the difference in the diameters of the two pores is less than about 20% of the larger diameter. Typically, the mean diameter of the pores is between about 20 and about 90 micrometers, such as between about 25 and 75 micrometers or between about 30 and 60 micrometers. In some embodiments, the mean diameter of the pores is between about 30 and 40 micrometers.

The pores may have any suitable shape. For example, the pores may be roughly, or perfectly, spherical, as shown in EXAMPLE 1. Other suitable pore shapes include, but are not limited to, dodecahedrons (such as pentagonal dodecahedons), and ellipsoids. In some embodiments, substantially all the pores have a roundness of at least about 0.1, such as at least about 0.3 or at least about 0.7. As used herein, "roundness" is defined as $(6 \times V)/(pi \times D^3)$, where V is the volume and D is the diameter. For example, a sphere has a roundness equal to 1.

In the array of pores, substantially all the pores are each connected to at least four other pores. In some embodiments, substantially all the pores are connected to between about 4 to 12 other pores, such as between about 4 to 7 other pores. Substantially all the connections between the pores have a diameter that is between about 15% and about 40%, such as between about 25% and about 30%, of the mean diameter of the pores. As used herein, the term "diameter of the connection between the pores" refers to the diameter of the cross-section of the connection between two pores in the plane normal to the line connecting the centroids of the two pores, where the plane is chosen so that the area of the cross-section of the connection is at its minimum value. The term "diameter of a cross-section of a connection" refers to the average length of a straight line segment that passes through the center, or centroid (in the case of a connection having a cross-section that lacks a center), of the cross-section of a connection and terminates at the periphery of the cross-section. The term "substantially all the connections" refers to at least 90% of the connections in the biomaterial, such as at least 95% or at least 97% of the connections.

Figure 3:
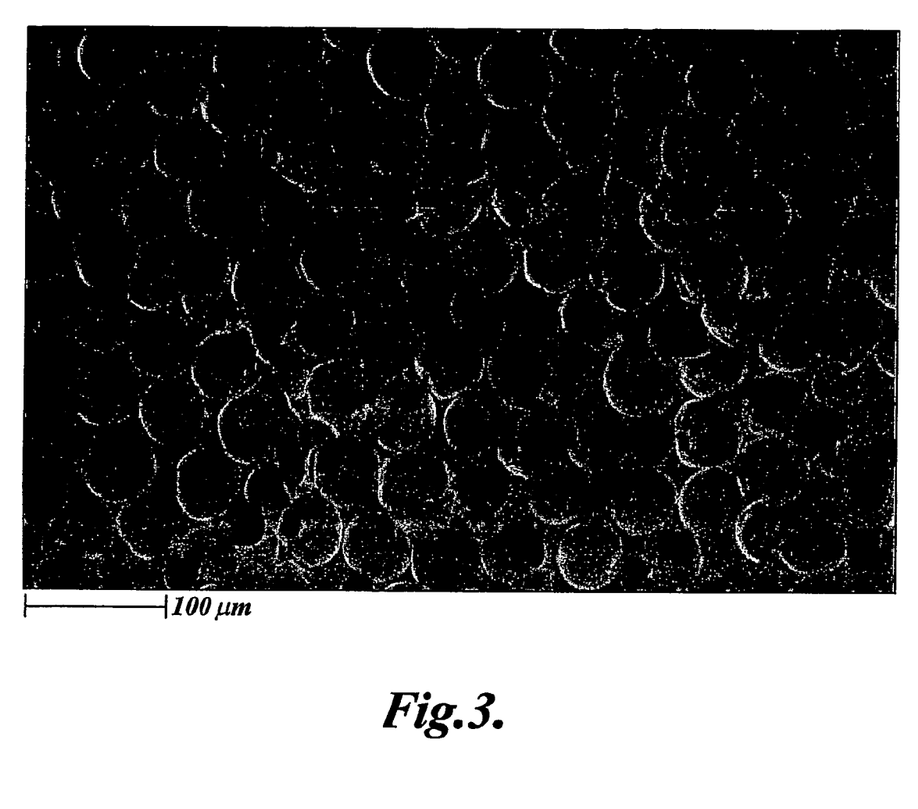
FIG. 3 shows a scanning electron micrograph of an exemplary porous biomaterial of the invention.

The diameter and shape of the pores, as well as the connections between them may be assessed using scanning electron microscopy, as described in EXAMPLE 1. FIG. 3 shows a scanning electron micrograph of an exemplary porous biomaterial of the invention.

The porous biomaterials of the invention allow a high degree of blood vessel formation inside the biomaterial when implanted into a host, as described in EXAMPLE 2. The biomaterials of the invention are useful for many applications, including, but not limited to, tissue engineering and repair. For example, the biomaterials may be applied as a wound dressing, as an artificial skin substitute for the treatment of burns and wounds. In some embodiments, hydroxyapatite is added to the polymer scaffold for use in bone repair and bone tissue engineering.

In some embodiments, the invention provides implantable devices comprising a layer of a biomaterial, wherein the biomaterial comprises a biocompatible polymer scaffold surrounding an array of pores, wherein substantially all the pores have a similar diameter, wherein the mean diameter of the pores is between about 20 and about 90 micrometers, wherein substantially all pores are each connected to at least 4 other pores, and wherein the diameter of substantially all the connections between the pores is between about 15% and about 40% of the mean diameter of the pores.

The biomaterial in or on the implantable devices of the invention are as described above. In some embodiments, the layer of biomaterial has a thickness of at least 70 micrometers. For example, the layer of biomaterial may have a thickness between about 100 and 1000 micrometers, such as between about 100 micrometers and about 500 micrometers.

The implantable devices may be any implantable medical devices, including, but not limited to, chemical sensors or biosensors (such as devices for the detection of analyte concentrations in a biological sample), cell transplantation devices, drug delivery devices such as controlled drug-release systems, electrical signal delivering or measuring devices, prosthetic devices, and artificial organs. The layer of biomaterial improves the biocompatibility of the implanted medical device (such as the biocompatibility and communication of neuroelectrodes and pacemaker leads with surrounding tissues), improves the sealing of skin to percutaneous devices (such as in-dwelling catheters or trans-cutaneous glucose sensors), enhances tissue integration, and provides barriers for immunoisolation of cells in artificial organs systems (such as pancreatic cells devices), and to improve the healing of vessels after balloon angioplasty and stent placement.

In some embodiments, the devices of the invention comprise a device body, wherein the porous biomaterial is attached to the device body. Some embodiments provide medical devices comprising a device body and a porous biomaterial of the invention attached to the device body. The porous biomaterial may be immobilized onto (or within) a surface of an implantable or attachable medical device body. In some embodiments, the porous biomaterial is attached to the outer surface of the device body. For example, the porous biomaterial may be disposed over substantially the entire outer surface of the device body. The modified surface will typically be in contact with living tissue after implantation into an animal body. As used herein, "implantable or attachable medical device" refers to any device that is implanted into, or attached to, tissue of an animal body, during the normal operation of the device (e.g., implantable drug delivery devices). Such implantable or attachable medical device bodies can be made from, for example, nitrocellulose, diazocellulose, glass, polystyrene, polyvinylchloride, polypropylene, polyethylene, dextran, Sepharose, agar, starch, and nylon. Linkage of the porous biomaterial to a device body can be accomplished by any technique that does not destroy the desired properties of the porous biomaterial. For example, a surface of an implantable or attachable medical device body can be modified to include functional groups (e.g., carboxyl, amide, amino, ether, hydroxyl, cyano, nitrido, sulfanamido, acetylinic, epoxide, silanic, anhydric, succinimic, azido) for immobilizing a porous biomaterial thereto. Coupling chemistries include, but are not limited to, the formation of esters, ethers, amides, azido and sulfanamido derivatives, cyanate and other linkages to functional groups available on the porous biomaterial.

In some embodiments, a surface of a device body that does not possess useful reactive groups can be treated with radiofrequency discharge plasma (RFGD) etching to generate reactive groups (e.g., treatment with oxygen plasma to introduce oxygen-containing groups; treatment with propyl amino plasma to introduce amine groups). When RFGD glow discharge plasma is created using an organic vapor, deposition of a polymeric overlayer occurs on the exposed surface. RFGD plasma deposited films offer several unique advantages. They are smooth, conformal, and uniform. Film thickness is easily controlled and ultrathin films (10-1000 Angstroms) are readily achieved, allowing for surface modification of a material without alteration to its bulk properties. Moreover, plasma films are highly-crosslinked and pin-hole free, and therefore chemically stable and mechanically durable. RFGD plasma deposition of organic thin films has been used in microelectronic fabrication, adhesion promotion, corrosion protection, permeation control, as well as biomaterials (see, e.g., U.S. Pat. No. 6,131,580).

Some medical devices of the invention are adapted to be implanted into the soft tissue of an animal, such as a mammal, including a human, during the normal operation of the medical device. Implantable medical devices of the invention may be completely implanted into the soft tissue of an animal body (i.e., the entire device is implanted within the body), or the device may be partially implanted into an animal body (i.e., only part of the device is implanted within an animal body, the remainder of the device being located outside of the animal body). Representative examples of completely implantable medical devices include, but are not limited to: cardiovascular devices (such as vascular grafts and stents), artificial blood vessels, artificial bone joints, such as hip joints, and scaffolds that support tissue growth (in such anatomical structures as nerves, pancreas, eye and muscle). Representative examples of partially implantable medical devices include: biosensors (such as those used to monitor the level of drugs within a living body, or the level of blood glucose in a diabetic patient) and percutaneous devices (such as catheters) that penetrate the skin and link a living body to a medical device, such as a kidney dialysis machine.

Some medical devices of the invention are adapted to be affixed to soft tissue of an animal, such as a mammal, including a human, during the normal operation of the medical device. These medical devices are typically affixed to the skin of an animal body. Examples of medical devices that are adapted to be affixed to soft tissue of an animal include skin substitutes, and wound or burn treatment devices (such as surgical bandages and transdermal patches).

Figure 1:
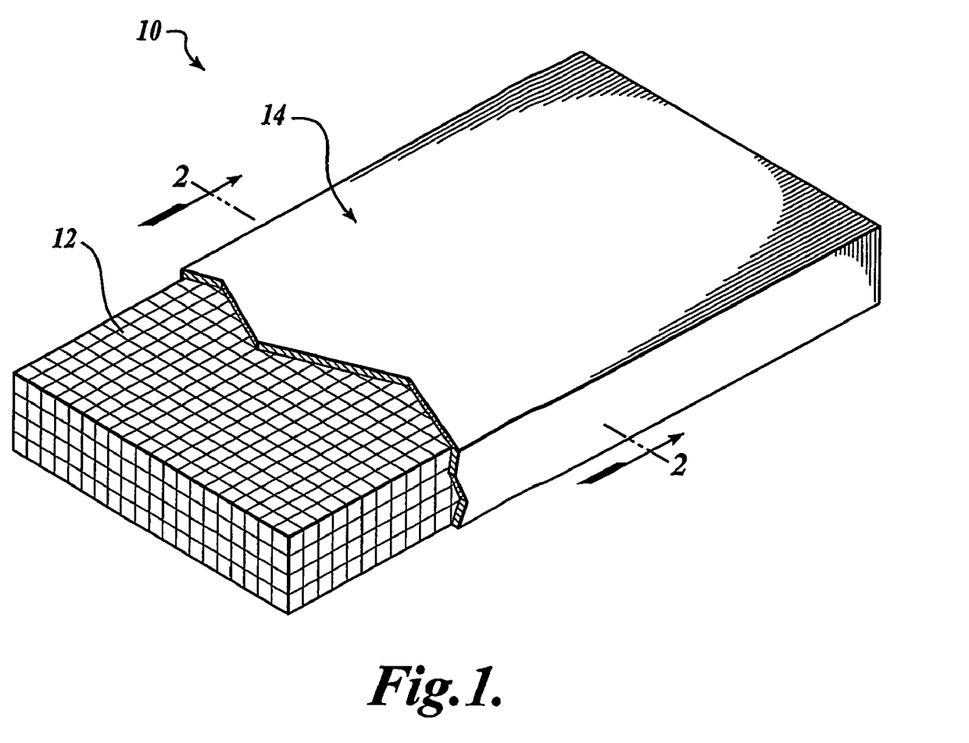
FIG. 1 shows a perspective view of a representative medical device of the invention with a portion of the porous biomaterial layer removed to expose the underlying device body.

FIG. 1 shows a representative medical device 10 of the present invention, in the form of an implantable drug delivery device, which includes a device body 12 to which is attached a porous biomaterial layer 14. In the embodiment shown in FIG. 1, porous biomaterial layer 14 has been partially removed to show device body 12 beneath. Device body 12 is indicated by hatching. As shown in the cross-sectional view of medical device 10 in FIG. 2, porous biomaterial layer 14 includes an internal surface 18, attached to device body 12, and an external surface 20.

Figure 2:
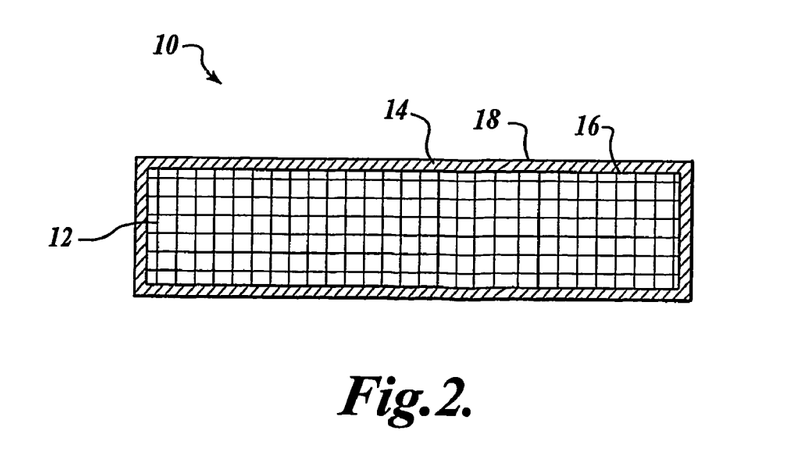
FIG. 2 shows a transverse cross-section of the medical device of FIG. 1.

Due to the biocompatibility of the porous biomaterials of the invention used in the construction of medical device 10, the presence of the porous biomaterial on the device body of a medical device will reduce or eliminate the foreign body response to the device body after implantation into, or attachment to, tissue of an animal body.

In some embodiments, the medical devices of the invention further comprise biologically active molecules within the porous biomaterial attached to the device body to provide for the controlled delivery of drugs and other biologically active molecules, such as DNA, RNA, or proteins. The biologically active molecules may be attached, covalently or non-covalently, to the crosslinking molecules or polymer molecules in the porous biomaterial.

Any reactive functional group present on polymer molecules within the porous biomaterial can be used to covalently attach biologically active molecules to the porous biomaterial. The following publications, incorporated herein by reference, describe examples of technologies that are useful for attaching biologically active molecules to polymer molecules, such as the polymers present in the porous biomaterial of the present invention: Nuttelman et al. (2001) *J. Biomed. Mater. Res.* 57:217-223; Rowley et al. (1999) *Biomaterials* 20:45-53; Hubbel (1995) *Biotechnology* 13:565-76; Massia & Hubbell (1990) *Anal. Biochem.* 187:292-301; Drumheller et al. (1994) *Anal. Biochem.* 222:380-8; Kobayashi & Ikada (1991) *Curr. Eye Res.* 10:899-908; Lin et al. (1992) *J. Biomaterial Sci. Polym. Ed.* 3:217-227; and Bellamkonda et al. (1995) *J. Biomed. Mater. Res.* 29:663-71.

The biologically active molecules may also be introduced into the porous biomaterial by forming the porous biomaterial in the presence of the biologically active molecules, by allowing the biologically active molecules to diffuse into a porous biomaterial, or by otherwise introducing the biologically active molecules into the porous biomaterial.

The biologically active molecules can be attached to every part of the device, or to only a portion of the device. For example, in some embodiments, that are adapted to be implanted into an animal, biologically active molecules that act to decrease the foreign body reaction (e.g., anti-inflammatory agents, and immunomodulatory agents) are attached only to the surface(s) of the device that is/are in contact with living tissue in the animal body. The biologically active molecules serve to decrease the foreign body reaction of the living body against the implanted structure.

Another aspect of the invention provides methods for forming porous biomaterials. The methods comprise the steps of: (a) forming a biocompatible polymer scaffold around a template comprising an array of monodisperse porogens, wherein substantially all the porogens have a similar diameter, wherein the mean diameter of the porogens is between about 20 and about 90 micrometers, wherein substantially all porogens are each connected to at least 4 other porogens, and wherein the diameter of substantially all the connections between the porogens is between about 15% and about 40% of the mean diameter of the porogens; and (b) removing the template to produce a porous biomaterial.

The template used in the methods of the invention comprises an array of porogens. As used herein, the term "porogens" refers to any structures that can be used to create a template that is removable after the biocompatible polymer scaffold is formed under conditions that do not destroy the polymer scaffold. Exemplary porogens that are suitable for use in the methods of the invention include, but are not limited to, polymer particles such as PMMA beads and polystyrene beads.

The porogens may have any suitable shape that will permit the formation of a porous biomaterial with an array of pores, wherein substantially all the pores have a similar diameter, wherein the mean pore diameter is between about 20 and about 90 micrometers, wherein substantially all pores are each connected to at least 4 other pores, and wherein the diameter of substantially all the connections between the pores is between about 15% and about 40% of the mean diameter of the pores. For example, the porogens may be spherical, as shown in EXAMPLE 1. Other suitable porogen shapes include, but are not limited to, dodecahedrons (such as pentagonal dodecahedons), and ellipsoids. In some embodiments, substantially all the porogens have a roundness of at least about 0.1, such as at least about 0.3 or at least about 0.7. "Roundness" is defined as described above.

Substantially all the porogens in the array have a similar diameter. As used herein, the term "substantially all the porogens" refers to at least 90% of the porogens, such as at least 95% or at least 97% of the porogens. As used herein, "diameter of the porogen" is defined as the longest line segment that can be drawn that connects two points within the porogen, regardless of whether the line passes outside the boundary of the porogen.

Two porogens have a "similar diameter" when the difference in the diameters of the two porogens is less than about 20% of the larger diameter. Porogens having similar diameters of a desired size may be obtained by size fractionation, as described, for example, in EXAMPLE 1. Typically, the mean diameter of the porogens is between about 20 and about 90 micrometers, such as between about 25 and 75 micrometers or between about 30 and 60 micrometers. In some embodiments, the mean diameter of the porogens is between about 30 and 40 micrometers.

In the array of porogens, substantially all the porogens are each connected to at least 4 other porogens. In some embodiments, substantially all the porogens are connected to between about 4 to 12 other porogens, such as between about 4 to 7 other porogens. Substantially all the connections between porogens have a diameter that is between about 15% and about 40%, such as between about 25% and about 30%, of the mean diameter of the porogens. The term "substantially all the connections" refers to at least 90% of the connections in the array of porogens, such as at least 95% of the connections or at least 97% of the connections.

In some embodiments, the invention provides methods for forming the template. The methods may comprise packing the porogens into a mold. Any mold may be used for packing the porogens. For example, a suitable mold may be formed using two glass microscope slides separated by 1-mm or 3-mm spacers. The porogens may be packed into a mold using ultrasonic agitation, or any other suitable method for obtaining a closely packed array of porogens.

In some embodiments, the methods for forming the template comprise fusing the porogens to form the connections between the porogens. The porogens may be fused by sintering. Typically, the sintering temperature is higher than the glass transition temperature of the polymer, such as between about 10° C. and about 50° C. higher than the glass transition temperature of the polymer. Increasing the duration of the sintering step at a given temperature increases the connection size; increasing the sintering temperature increases the growth rate of the connections. Suitable sintering times are generally between 1 and 48 hours. In some embodiments, PMMA beads are sintered for 19 hours at 140° C. to produce connection diameters of about 30% of the diameter of the beads, as described in EXAMPLE 1. The porogens can also be fused by other methods. For example, the porogens can be fused by partially dissolving them by treatment with a suitable solvent.

Once a template has been created, a biocompatible polymer scaffold is formed around the template. Suitable biocompatible polymers are as described above. In some embodiments, the polymer scaffold is formed around the template by polymerizing a polymer precursor mixture around the template. The polymer precursor mixture typically comprises polymer precursors and suitable cross-linking reagents, as described in EXAMPLE 1.

After a biocompatible polymer scaffold has been formed, the template is removed to produce the porous biomaterial. In some embodiments, the template is removed by solvent extraction. For example, PMMA beads may be extracted with a 9:1 v/v acetone-water solution, as described in EXAMPLE 1. The porous biomaterials formed using the methods of the invention comprise an array of uniformly shaped pores, as shown in FIG. 3.

In a further aspect, the invention provides methods for promoting angiogenesis in and around an implantable biomaterial. The methods comprise the step of implanting a porous biomaterial, wherein the biomaterial comprises a biocompatible polymer scaffold surrounding an array of pores, wherein substantially all the pores have a similar diameter, wherein the mean diameter of the pores is between about 20 and about 90 micrometers, wherein substantially all pores are each connected to at least 4 other pores, and wherein the diameter of substantially all the connections between the pores is between about 15% and about 40% of the mean diameter of the pores. The biomaterials used in the methods for promoting angiogenesis are as described above. As shown in EXAMPLE 2, the porous biomaterials of the invention promote the growth of blood vessels into the biomaterials.

The following examples illustrate representative embodiments now contemplated for practicing the invention, but should not be construed to limit the invention.

EXAMPLE 1

This Example describes an exemplary method of the invention for making biomaterials with tightly controlled pore diameters.

Materials: Poly(methyl methacrylate) (PMMA) beads with diameter less than 100 micrometers were purchased from Kupa, Inc (Product No. BN-PW-CC). Larger beads were obtained from Polysciences (25,000 MW), along with 2-hydroxyethyl methacrylate (ophthalmic grade), ethylene glycol, and tetraethylene glycol dimethacrylate. 2,2-dimethoxy-2-phenylacetophenone was purchased from Ciba-Geigy. Poly($\epsilon$-caprolactone) diol ($M_n$~530) and all other chemicals were acquired from Aldrich Non-porous silicone rubber was purchased from Invotec Intl. (Cat No. 20-10680). Sieves of the desired opening sizes were custom made with stainless steel meshes purchased from McMaster-Carr. All materials were used as received unless otherwise specified.

Implant Fabrication: PMMA beads were thoroughly fractionated to the desired sizes (20±5 μm, 35±5 μm, 50±5 μm, 70±5 μm, 90±5 μm and 160±15 μm) with an ATM Model L3P Sonic Sifter. Each bead size was separated with an iterative process, with an iteration comprising the following steps: (1) the beads were sieved for approximately 10 minutes; (2) the beads were decanted from the sieves; and the fractions were labeled; (3) the monodispersity of the beads was examined by light microscopy after attaching a monolayer of beads to a slide with transparent tape; (4) the meshes were unclogged by blowing from underneath with compressed air; and (5) the beads were replaced on the same sieves from which they were removed. Five to six iterations were required for each bead size to yield size fractions with the above tolerances. The beads were added to molds consisting of two microscope slides separated by nylon spacers, packed by ultrasonic agitation, and sintered for 19 hours at 140° C. to give neck sizes of 30% of the bead diameter. These fused-bead pore templates were infiltrated with a polymer precursor comprising the components in Table 1.

TABLE 1

Polymer Precursor Mixture

| Component | Volume (mL) |
|---|---|
| 2-hydroxyethyl methacrylate (HEMA) | 7.0 |
| Ethylene glycol | 2.1 |
| Water | 0.9 |
| Tetraethylene glycol dimethacrylate | 0.31 |
| Type I collagen in 0.02 N acetic acid (4 mg/mL) | 0.5 |
| Ammonium persulfate (0.4 g/mL) | 0.7 |
| Sodium metabisulfite (0.15 g/mL) | 0.7 |

After allowing the mixture to polymerize for 24 hours, the PMMA templates were extracted with a 9:1 v/v acetone-water solution to yield cross-linked porous hydrogel slabs of polyHEMA doped with Type I collagen. The slabs were punched into 4-mm disks, sterilized in 70% ethanol, rinsed every 24 hours for 1 week with endotoxin-filtered sterile water, and stored in sterile phosphate-buffered saline until use.

Degradable Cross-Linker Synthesis: Methacryloyl chloride was distilled at 30 mm Hg and 24° C. Then 4.0 g of vacuum-dried poly($\epsilon$-caprolactone) diol was dissolved in 34 mL of dry methylene chloride. Residual moisture was removed with molecular sieves. The solution was added to a 250-mL flask containing a dry nitrogen atmosphere at 0° C. Next, 1.25 molar excess (2.78 mL) of triethylamine was added to the flask, followed by dropwise addition of 1.25 molar excess (1.92 mL) of freshly distilled methacryloyl chloride diluted with 6 mL of dry methylene chloride. The reaction mixture was stirred for 8 hours at 0° C. The precipitated salt (triethylamine hydrochloride) was filtered off. Then unreacted triethylamine was removed by extracting with 1% hydrochloric acid until the aqueous layer remained colorless. Next, any methacrylic acid was removed by extracting with 3% sodium hydroxide until the aqueous layer remained colorless. The excess base was removed by repeated rinses with deionized water. The methylene chloride was evaporated to yield a white paste that melts into a colorless, viscous liquid at 25° C. The purity was verified by $^1$H-NMR and infrared spectroscopy.

Degradable Porous Hydrogel Preparation: HEMA monomer was purified by diluting 1:1 with water and extracting 4 times with hexane. Sodium chloride was then added until saturation, so that the HEMA separated out as the top layer. The HEMA layer was dried with sodium sulfate after diluting 1:1 with methylene chloride. Finally, the methylene chloride was evaporated. The monomer was verified to be dimethacrylatefree by polymerizing it into a linear hydrogel and solubilizing in 1:1 v/v acetone-methanol.

PMMA fused-bead pore templates (described earlier) were infiltrated with a polymer precursor consisting of the components in Table 2, and the mixture was irradiated with 365 nm UV light (UVP, Model UVGL-25) for 45 minutes. Then the pore templates were removed as described earlier, and the porous gels were verified to degrade completely within 2 weeks in 1 M sodium hydroxide at 37° C.

TABLE 2

Degradable Hydrogel Precursor Mixture

| Component | Volume (mL) |
|---|---|
| Purified 2-hydroxyethyl methacrylate (HEMA) | 7.0 mL |
| Ethylene glycol | 2.1 mL |
| Water | 0.9 mL |
| Ethanol | 0.02 mL |
| Poly($\epsilon$-caprolactone) dimethacrylate | 0.62 mL |
| Type I collagen in 0.02 N acetic acid (4 mg/mL) | 0.5 mL |
| 2,2-dimethoxy-2-phenylacetophenone | 0.07 g |

Scanning Electron Microscopy: Scanning Electron Microscopy (SEM) images were acquired with an FEI Sirion field emission electron microscope with no sample coatings and an accelerating voltage of 1 kV.

Results: All peaks in the 200-Hz proton NMR spectrum of the synthesized poly($\epsilon$-caprolactone dimethacrylate) are consistent with a successful high-yield synthesis. For many of the hydrogen types, there are two peaks, with the secondary peak shifted slightly downfield from the primary peak; this is especially noticeable for hydrogen types a and b. The primary peak corresponds to the case where there are two or more caprolactone units on the end of the molecule, while the smaller peak corresponds to the less abundant structure with one caprolactone unit on the end.

Prior to assembly of the templates, the monodispersity of each bead size of the PMMA beads was examined by light microscopy. For each bead size, at least 95% of the beads had a diameter equal to the mean bead diameter +/−20%.

The monodispersity of the necks in the porogen templates was measured from SEM images. For each bead size, at least 95% of the necks were verified to be between 25% and 35% of the mean bead diameter. Scanning Electron Microscopy was also used to determine the structure of the porous biomaterial. Examination of the SEM images revealed that each pore was connected to between 4 and 7 neighboring pores. The porous materials had a precisely uniform pore structure, as shown in FIG. 3.

EXAMPLE 2

This Example describes an in vivo analysis of the correlation between pore size in the biomaterials of the invention and the promotion of vascular in-growth.

Materials: Collagen and all antibodies were bought from BD Biosciences, mounting media (Permount) from Fisher.

Implantation and Histology: In experiment 1, disks (4-mm diameter, 1-mm thickness) of each of three porous materials (35-, 70-, and 160-μm pore diameter) made according to the method described in Example 1, along with a non-porous silicone rubber (Invotec Intl., Cat. No. 20-10680), were implanted subcutaneously into the dorsum of 7-month-old female mice (n=9). After 4 weeks, the implants were explanted, stabilized with methyl Carnoy's fixative, embedded in paraffin, cross-sectioned at the widest point, stained with an anti-mouse panendothelial cell antibody (MECA-32) in combination with biotinylated goat anti-rat IgG secondary antibody and avidin-biotin complex, developed with diaminobenzidine, and coverslipped with Permount. Sections were viewed in brightfield with a 4× objective, and imaged digitally. All intraimplant blood vessel profiles in each section were counted manually.

After analyzing results from experiment 1, materials with nominal pore diameters of 20, 35, 50, 70, and 90 μm were implanted in 3-month-old male mice and analyzed similarly (35-, 50-, 70-, and 90-μm pore sizes in experiment 2, and 20- and 35-μm pore sizes in experiment 3, with n=7 animals per group).

Results: As Table 3 illustrates, the number of blood vessels inside the pores increases as the pore diameter is decreased, reaching a maximum at a pore size of ~35 μm. The 160-μm pore diameter material was almost completely avascular. The smoothly decreasing trend from 35 to 160 μm suggests a dose response, with the number of vessels roughly proportional to the internal surface area (which is inversely proportional to the pore diameter). Results from a separate in vivo experiment, where the collagen-doped 35-μm pore material was compared to a protein-free control, indicate that the materials are vascularized to the same extent regardless of whether protein is added. Ostensibly, the observed dose response is caused by the presence of the surface per se rather than by the protein additives in the surface.

The 20-μm pores showed a significant decrease in vessel density relative to the 35-μm pores. This may be due to the inability of host macrophage cells or fibroblasts to penetrate deeply into the smaller pore material, as these two materials have uniformly-sized pore throat diameters of 6 and 10 μm respectively. Macrophages, which are about 10 μm in size, are expected to be slowed substantially by 6-μm constrictions. This is supported by examination of the number of vessels as a function of depth within the implant. Materials with pore sizes 50 μm or larger had approximately the same vessel density in the core of the implant as they did near the perimeter, while the 35-μm pore material had much lower vessel density in the core; the 20-μm material generally had high vascular density near the surface, but was completely vessel-free in all cases at the implant core.

TABLE 3

Effect of Pore Diameter on Blood Vessel Density

| Spherical Pore Diameter (micrometers) | Experimental Group | Blood Vessel Density (Mean Vessel Profiles/mm$^2$ ± standard error) |
|---|---|---|
| 20 | 3 | 72 ± 24 |
| 35 | 1 | 257 ± 40 |
|  | 2 | 226 ± 34 |
|  | 3 | 157 ± 18 |
| 50 | 2 | 180 ± 15 |
| 70 | 1 | 125 ± 23 |
|  | 2 | 126 ± 25 |
| 90 | 2 | 75 ± 10 |
| 160 | 1 | 9 ± 1 |

A depth-profiled intra-implant vessel density as a function of pore diameter is shown in Table 4 for experiment 1, and in Table 5 for combined experiments 1, 2, and 3. The 35-μm pore material induced maximum number of intra-plant blood vessels. For 50-μm pores and larger, the vessel density is almost uniformly distributed through the entire 1-mm thickness of the implant.

TABLE 4

Effect of Pore Diameter on Blood Vessel Density at Different Depths for Experiment 1

| Spherical Pore Diameter (micrometers) | Depth from Implant Surface (micrometers) | Blood Vessel Density (Mean Vessel Profiles/mm$^2$ ± standard error) |
|---|---|---|
| 35 | 0-100 | 323 ± 100 |
|  | 100-200 | 308 ± 97 |
|  | 200-300 | 276 ± 91 |
|  | 300-400 | 232 ± 89 |
|  | 400-500 | 168 ± 63 |
| 70 | 0-100 | 109 ± 60 |
|  | 100-200 | 125 ± 49 |
|  | 200-300 | 137 ± 45 |
|  | 300-400 | 136 ± 47 |
|  | 400-500 | 114 ± 38 |
| 160 | 0-100 | 10 ± 3 |
|  | 100-200 | 9 ± 5 |
|  | 200-300 | 9 ± 3 |
|  | 300-400 | 8 ± 3 |
|  | 400-500 | 7 ± 2 |

TABLE 5

Effect of Pore Diameter on Blood Vessel Density at Different Depths for Combined Experiments 1, 2, and 3

| Spherical Pore Diameter (micrometers) | Depth from Implant Surface (micrometers) | Blood Vessel Density (Mean Vessel Profiles/mm$^2$ ± standard error) |
|---|---|---|
| 20 | 0-100 | 86 ± 27 |
|  | 100-200 | 104 ± 34 |
|  | 200-300 | 96 ± 37 |
|  | 300-400 | 66 ± 29 |
|  | 400-500 | 41 ± 27 |
| 35 | 0-100 | 246 ± 23 |
|  | 100-200 | 245 ± 23 |
|  | 200-300 | 217 ± 24 |
|  | 300-400 | 203 ± 22 |
|  | 400-500 | 178 ± 21 |
| 50 | 0-100 | 176 ± 23 |
|  | 100-200 | 188 ± 17 |
|  | 200-300 | 175 ± 19 |
|  | 300-400 | 173 ± 18 |

TABLE 5-continued

Effect of Pore Diameter on Blood Vessel Density at Different Depths for Combined Experiments 1, 2, and 3

| Spherical Pore Diameter (micrometers) | Depth from Implant Surface (micrometers) | Blood Vessel Density (Mean Vessel Profiles/mm² ± standard error) |
|---|---|---|
|  | 400-500 | 172 ± 25 |
| 70 | 0-100 | 110 ± 17 |
|  | 100-200 | 130 ± 17 |
|  | 200-300 | 137 ± 17 |
|  | 300-400 | 133 ± 17 |
|  | 400-500 | 120 ± 15 |
| 90 | 0-100 | 86 ± 7 |
|  | 100-200 | 87 ± 10 |
|  | 200-300 | 73 ± 14 |
|  | 300-400 | 77 ± 10 |
|  | 400-500 | 64 ± 11 |
| 160 | 0-100 | 10 ± 3 |
|  | 100-200 | 9 ± 5 |
|  | 200-300 | 9 ± 3 |
|  | 300-400 | 8 ± 3 |
|  | 400-500 | 7 ± 2 |

The mean vessel density as a function of pore diameter is shown in Table 6. These data can be fit ($R^2=0.998$) with an expression of the form:

$$N_{vessels} = k_1/d_{pore} \text{ minus } k_2/d^2_{throat} \text{ minus } k_0$$

where $N_{vessels}$ is the vessel density, $k_1$, $k_2$, and $k_0$ are fitting constants, $d_{pore}$ is the spherical pore diameter, and $d_{throat}$ is the pore throat diameter.

TABLE 6

Mean Vessel Density as a Function of Pore Diameter

| Spherical Pore Diameter (micrometers) | Blood Vessel Density (Mean Vessel Profiles/mm² ± standard error) |
|---|---|
| 20 | 70 ± 26 |
| 35 | 217 ± 22 |
| 50 | 176 ± 18 |
| 70 | 126 ± 15 |
| 90 | 75 ± 10 |
| 160 | 9 ± 2 |

The mean vessel density as a function of surface area is shown in Table 7. The specific surface area (i.e., the surface area per unit volume) is inversely proportional to pore size and can be easily calculated when the average pore size and pore geometry are known. When the data are plotted as a function of specific surface area, the curve fit takes the form of a second order parabola.

TABLE 7

Mean Vessel Density as a Function of Surface Area

| Specific Surface Area (cm²/cm³) | Blood Vessel Density (Mean Vessel Profiles/mm² ± standard error) |
|---|---|
| 217 | 9 ± 2 |
| 387 | 75 ± 10 |
| 497 | 126 ± 15 |
| 696 | 176 ± 18 |
| 994 | 217 ± 22 |
| 1740 | 70 ± 26 |

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A biomaterial, comprising a biocompatible polymer scaffold defining an array of pores, wherein substantially all the pores have a similar diameter, wherein the mean diameter of the pores is between about 20 and about 90 micrometers, wherein substantially all the pores are each connected to at least 4 other pores, and wherein the diameter of substantially all the connections between the pores is between about 15% and about 40% of the mean diameter of the pores, wherein the biocompatible polymer scaffold comprises silicone rubber.

2. The biomaterial of claim 1, wherein the mean pore diameter is between about 30 and about 40 micrometers.

3. The biomaterial of claim 1, wherein the biocompatible polymer scaffold is a hydrogel.

4. The biomaterial of claim 1, wherein the biomaterial has a thickness of at least 70 micrometers.

5. An implantable device, comprising a layer of a biomaterial, wherein the biomaterial comprises a biocompatible polymer scaffold surrounding an array of monodispersed pores, wherein substantially all the pores have a similar diameter, wherein the mean diameter of the pores is between about 20 and about 90 micrometers, wherein substantially all pores are each connected to at least 4 other pores, and wherein the diameter of substantially all the connections between the pores is between about 15% and about 40% of the mean diameter of the pores, wherein the biocompatible polymer scaffold comprises silicone rubber.

6. The implantable device of claim 5, wherein the layer of biomaterial has a thickness of at least 70 micrometers.

7. The device of claim 5, wherein the device comprises a device body, wherein the layer of biomaterial is attached to the device body.

8. The device of claim 7, wherein the layer of biomaterial is attached to the outer surface of the device body.

9. The device of claim 7, wherein the device is a medical device.

10. A method for forming a biomaterial, comprising the steps of:
    (a) forming a biocompatible polymer scaffold around a template comprising an array of monodisperse porogens, wherein substantially all the porogens have a similar diameter, wherein the mean diameter of the porogens is between about 20 and about 90 micrometers, wherein substantially all porogens are each connected to at least 4 other porogens, and wherein the diameter of substantially all the connections between the porogens is between about 15% and about 40% of the mean diameter of the porogens, wherein the biocompatible polymer scaffold comprises silicone rubber; and
    (b) removing the template to produce a porous biomaterial.

11. The method of claim 10, wherein the porogens are spherical beads.

12. The method of claim 10, wherein the porogens comprise poly(methyl) methacrylate.

13. The method of claim 10, wherein the biomaterial has a thickness of at least 70 micrometers.

14. The method of claim 10, wherein step (a) comprises forming the template by packing the porogens into a mold and fusing the porogens to form the connections between the porogens.

15. The method of claim 14, wherein the porogens are fused by sintering.

16. A method for promoting angiogenesis in and around an implantable biomaterial, comprising the step of implanting a porous biomaterial, wherein the biomaterial comprises a biocompatible polymer scaffold surrounding an array of pores, wherein substantially all the pores have a similar diameter, wherein the mean diameter of the pores is between about 20 and about 90 micrometers, wherein substantially all pores are each connected to at least 4 other pores, and wherein the diameter of substantially all the connections between the pores is between about 15% and about 40% of the mean diameter of the pores, wherein the biocompatible polymer scaffold comprises silicone rubber.

17. A biomaterial, comprising a biocompatible polymer scaffold defining an array of pores, wherein substantially all the pores have a similar diameter, wherein the mean diameter of the pores is between about 20 and about 90 micrometers, wherein substantially all the pores are each connected to at least 4 other pores, and wherein the diameter of substantially all the connections between the pores is between about 15% and about 40% of the mean diameter of the pores, wherein the biocompatible polymer scaffold comprises collagen.

18. An implantable device, comprising a layer of a biomaterial, wherein the biomaterial comprises a biocompatible polymer scaffold surrounding an array of monodispersed pores, wherein substantially all the pores have a similar diameter, wherein the mean diameter of the pores is between about 20 and about 90 micrometers, wherein substantially all pores are each connected to at least 4 other pores, and wherein the diameter of substantially all the connections between the pores is between about 15% and about 40% of the mean diameter of the pores, wherein the biocompatible polymer scaffold comprises collagen.

19. A method for forming a biomaterial, comprising the steps of:
 (a) forming a biocompatible polymer scaffold around a template comprising an array of monodisperse porogens, wherein substantially all the porogens have a similar diameter, wherein the mean diameter of the porogens is between about 20 and about 90 micrometers, wherein substantially all porogens are each connected to at least 4 other porogens, and wherein the diameter of substantially all the connections between the porogens is between about 15% and about 40% of the mean diameter of the porogens, wherein the biocompatible polymer scaffold comprises collagen; and
 (b) removing the template to produce a porous biomaterial.

20. A method for promoting angiogenesis in and around an implantable biomaterial, comprising the step of implanting a porous biomaterial, wherein the biomaterial comprises a biocompatible polymer scaffold surrounding an array of pores, wherein substantially all the pores have a similar diameter, wherein the mean diameter of the pores is between about 20 and about 90 micrometers, wherein substantially all pores are each connected to at least 4 other pores, and wherein the diameter of substantially all the connections between the pores is between about 15% and about 40% of the mean diameter of the pores, wherein the biocompatible polymer scaffold comprises collagen.

* * * * *